Feb. 1, 1938. G. DE RUYTER Plant Pat. 270
ROSE
Filed April 14, 1937
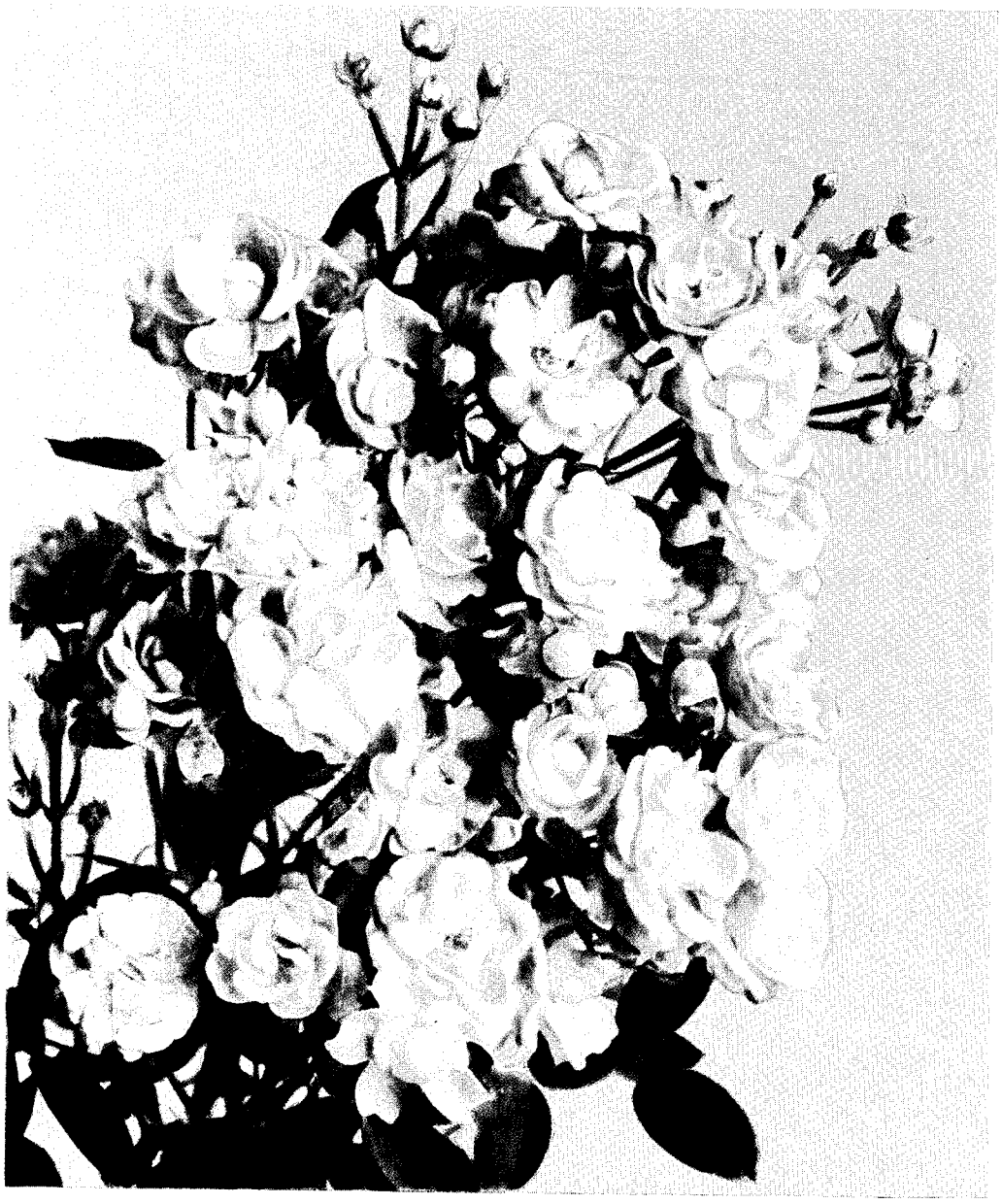
Inventor
Gerrit de Ruyter
By Robert Robb
attorneys Patented Feb. 1, 1938

UNITED STATES PATENT OFFICE

270

ROSE

Gerrit de Ruyter, Hazerswonde, Netherlands, assignor to Jackson & Perkins Company, Newark, N. Y.

Application April 14, 1937, Serial No. 136,920

1 Claim. (Cl. 47—61)

The present invention or discovery relates to a new and distinct variety of rose plant, originating as a sport of the well known variety "Gloria Mundi."

Because of the marked distinctions from its parent and other varieties, as hereinafter set forth, the original sport was recognized as a new polyantha having a number of much to be desired characteristics, if they could be perpetuated, leading to a definite effort to preserve the same.

After reproducing by budding for several generations, the desired characteristics were fixed and now come true to form by asexual propagation, as tests made both in America and Europe have proved.

Primarily, the color of the new variety differs from that of "Gloria Mundi" in that while much softer, it is more brilliant and more lasting without change or burn when exposed to the sun.

Secondly, this color is more uniform than is true of the color of the parent rose. By reason of these distinctive color features, the new variety is especially desirable for the pot trade inasmuch as the florist can keep the plants in the height of color for a longer period of time than other varieties in the same range of colors.

Not only is this new variety distinguished from its parent by the color of its flowers primarily, but it is also distinguished to a greater degree with respect to all other roses by the peculiar coloring above referred to. In fact it may be noted that there is no standard chart at the present time which gives the true color of the rose. The color may be said to come within the range of "orange scarlet", referring to the Gravereaux standard, and might be described as "scarlet" heavily suffused or veiled with "orange". Using the Gravereaux scale, the color, by way of comparison, might be arrived at by taking the color "flame", Plate 2, No. 1 of column 3 (see The Rose Manual by Nicolas) and superimposing upon it a yellow wash. The drawing herewith shows the color as nearly as it can be depicted.

A further point of distinction is the improved growing habit of the plant by which it presents a more compact and attractive form.

The following is a detail description of the new variety:—(Colors refer to Gravereaux chart except where obviously dictionary definitions are meant.)

Parentage:

Sport.

*Parent variety.*—"Gloria Mundi."

Classification:

*Botanic and commercial.*—Polyantha.

*Flower*

Blooming habit:

Location where observations were made—Jackson & Perkins Co. Nurseries, Newark, N. Y.

*Recurrent.*—Continuous.

Bud:

*Size.*—Small.

*Form.*—Ovoid. Not affected by wet or hot weather.

*Color.*—Scarlet with heavy suffusion of orange.

*Sepals.*—Smooth edge, stand up.

*Calyx.*—Shape—pear. Size—small. Aspect—glandular. No odor when rubbed.

*Peduncle.*—Length — short. Aspect — rough. Color—medium green and bronzy. Strength—stiff, slender.

*Opening.*—Bud opens well. Is not affected by adverse conditions.

Bloom:

*Size.*—Small. Average size when fully expanded—1¼ in.

*Borne.*—In rounded clusters.

*Stems.*—Medium length, strong.

*Form.*—Cupped, retains its form to the end.

*Petalage.*—Double (full but open center).

*Color.*—Scarlet with heavy orange suffusion or veiling.

*Variegations.*—None.

*Discoloration.*—General tonality at end of first, second and third days is scarlet with heavy orange suffusion.

Petals:

*Texture.*—Thick. Unaffected by wet or hot weather.

*Appearance.*—Inside and outside—satiny.

*Form.*—Round.

*Arrangement.*—Imbricated (regularly arranged shingle-like). Petaloids in center—none.

*Persistence.*—Drop off cleanly.

*Fragrance.*—None.

*Lasting quality.*—On the plant and as cut flower—very long.

Genital organs:

*Stamens, anthers.*—Small, many. Color—lemon. Arrangement—regular around styles.

*Stamens, filaments (threads).*—Medium. Color—lemon.

*Pollen.*—Lemon yellow.

*Styles.*—Loosely separated, even length. Short, heavy.

*Stigmas.*—Color—lemon.

*Ovaries.*—All enclosed in calyx.

Fruit:

Variety is fertile with its own pollen.

*Form.*—Round.
*Aspect.*—Smooth.
*Color at maturity.*—Scarlet.
*Sepals.*—Caducous (soon falling).

*Plant*

Form: Bush.
Growth: Medium.
Foliage:
3, 5, 7 leaflets—mostly seven.
*Size.*—Small.
*Quantity.*—Abundant.
*Color.*—*New foliage*—Upper side—dark green. Under side—lighter green. *Old foliage*—Upper side—dark green. Under side—lighter green.
*Shape.*—Lanceolate.
*Texture.*—Upper side—glossy. Under side—smooth. Ribs and veins—ordinary.
*Edge.*—Serrated (saw toothed).
*Serration.*—Small.
*Rachis.*—Color—reddish. Under side—smooth.
*Stipules.*—Medium, bearded.
*Disease resistance.*—Resistant.
Wood:
*New wood.*—Color—reddish. Bark—rough.
*Old wood.*—Color—brown. Bark—rough.
Thorns: (Thorns are divided into thorns, prickles and short needles).
*Thorns.*—Quantity—on main stalks from base, many; on laterals from stalk, ordinary. Form—broad base, medium, hooked downward. Color when young—blood red. Position—irregular.
*Prickles.*—Quantity—on main stalks, many; on laterals, few. Color—brown.
*Short needles.*—Quantity—on main stalks, many; on laterals, none.

I claim:

A new and distinct variety of polyantha rose plant characterized by the distinctiveness, uniformity and permanence of the color of its bloom, as shown and described, and the improved compactness and attractive form of the plant, rendering it equally adaptable for garden use or forcing in pot.

GERRIT DE RUYTER.